United States Patent
Vahaviolos

[11] 4,004,456
[45] Jan. 25, 1977

[54] METHOD AND APPARATUS FOR THE REAL-TIME, NON-DESTRUCTIVE EVALUATION OF ADHESION BONDS USING STRESS-WAVE EMISSION TECHNIQUES

[75] Inventor: Sotirios John Vahaviolos, East Windsor Township, Mercer County, N.J.

[73] Assignee: Western Electric Company, Inc., New York, N.Y.

[22] Filed: Aug. 18, 1975

[21] Appl. No.: 605,489

[52] U.S. Cl. .................................................. 73/71.4
[51] Int. Cl.² ........................................ G01N 29/00
[58] Field of Search ................. 73/67 R, 71.4, 88.3; 228/103, 104

[56] References Cited
UNITED STATES PATENTS

| | | | |
|---|---|---|---|
| 3,713,127 | 1/1973 | Keledy et al. | 73/67 |
| 3,782,183 | 1/1974 | O'Connor et al. | 73/67 |
| 3,822,586 | 7/1974 | Pollock | 73/71.4 |

OTHER PUBLICATIONS

Beattie et al., "The Measurement of Energy in Acoustic Emission," in Review of Sci. Instruments, vol. 45, No. 3, Mar. 1974, pp. 352–357.
Jolly, "The Application of Acoustic Emission to In-Process Inspection of Welds," in Materials Evaluation, vol. 28, No. 6,7/70, pp. 135–139 & 144.
Pollock, "Acoustic Emission Methods of N.D.T.," in British Journal of N.D.T., vol. 13, No. 3, 5/71, pp. 85–89.

Primary Examiner—Herbert Goldstein
Attorney, Agent, or Firm—E. W. Pfeifle; D. J. Kirk

[57] ABSTRACT

The strength of an adhesion bond can be determined using stress-wave emission techniques. One method measures the stress-wave emitted from the bonding area during the compression phase of the formation of the bond and compares this measurement with a predetermined substantially linear relationship between the emitted stress-wave energy and the strength of the adhesion bond. For more accuracy, a second method measures the stress-wave energy during both the compression phase and a pressure-relief interval, determines the difference between the two measurements, and compares the difference value with the substantially linear relationship. An alternative to the second method subtracts a predetermined threshold value from the pressure-relief interval measurement, reduces the compression phase measurement by the excess determined by said subtraction step, and compares the reduced compression phase measurement with the predetermined substantially linear relationship to determine the strengh of the bond.

12 Claims, 6 Drawing Figures

METHOD AND APPARATUS FOR THE REAL-TIME, NON-DESTRUCTIVE EVALUATION OF ADHESION BONDS USING STRESS-WAVE EMISSION TECHNIQUES

BACKGROUND OF THE INVENTION

1. Field of the Invention

This invention relates to a method and apparatus for the real-time, non-destructive evaluation of adhesion bonds using stress-wave emission techniques, and more particularly, to method and apparatus for evaluating an adhesion bond by measuring the stress-wave energy emitted during the bonding cycle and comparing the measured energy with a predetermined substantially linear relationship between the emitted stress-wave energy and the strength of the adhesion bond to determine the strength of the bond.

2. Description of the Prior Art

The ability to evaluate the strength of an adhesion bond has in recent years become increasingly important with the increased use of thermocompression, ultrasonic and other bonding techniques. The most common method used for determining the strength of an adhesion bond is the standard peel test. Such test, however, destroys the bond and is, therefore, not a very desirable test, since it can only be used on a spot-check basis.

A method for non-destructively indicating the quality of an adhesion bond formed by vibratory bonding techniques is disclosed in U.S. Pat. No. 3,302,277, issued to D. H. Pruden et al. on Feb. 7, 1967. There, a test current is passed through an electrical component being bonded to an element and a change in the voltage drop across the bond area measured. The measured voltage drop is then used to indicate the quality of the bond, and alternatively to control the amount of vibratory energy introduced into the bonding zone.

Stress-wave emission detection and measuring techniques have been used for detecting low amplitude, short duration, and fast rise time pulses emitted by cracks forming in brittle materials when the material is subjected to a load as, for example, during a bonding operation or pressure test. In this regard, see, for example, a report dated May 19, 1972, entitled, "Investigation of Acoustic Emission from Ceramic-Materials," by G. A. Alers, No. SC 513.6FR, published by North American Rockwell Science Center.

U.S. Pat. No. 3,965,726, which issued on June 29, 1976 to the present inventor and is assigned to the same assignee, evaluates spot welds by measuring the stress waves emitted during various time periods of the welding cycle, each time period corresponding to a different aspect of the weld cycle such as, for example, the solid-to-liquid phase transformation and the liquid-to-solid phase transformation in the weld area since each of these elements, and others, can affect the quality and/or the extent of a weld. This patent also discloses that a relatively linear relationship exists between the net resultant stress-wave energy value which is the difference in energy between the solid-to-liquid and the liquid-to-solid phase transformations of a spot weld. The problem still remains of providing method and apparatus which is inexpensive and which non-destructively determines the strength of an adhesion bond in real time.

BRIEF SUMMARY OF THE INVENTION

The present invention relates to a method and apparatus for the real-time, non-destructive evaluation of an adhesion bond using stress-wave emission techniques, and more particularly, to a method and apparatus for evaluating an adhesion bond by measuring the stress-wave energy emitted during the formation of the bond and comparing the measured energy with a predetermined substantially linear relationship between the emitted stress-wave energy and the strength of the adhesion bond to determine the strength of the bond.

The present invention further relates to a method and apparatus for the real-time, non-destructive evaluation of adhesion bond by measuring the stress-wave energy during both the compression phase and a pressure-relief interval of the formation of a bond, and either, (a) determining the difference between the measurements obtained during each of the two intervals and thereafter comparing the difference value with a predetermined substantially linear relationship existing between the determined difference value and the strength of the adhesion bond; or (b) subtracting a predetermined threshold value from the pressure-relief measurement to obtain an excess value, reducing the obtained compression phase measurement by the excess value, and comparing the reduced compression-phase measurement with a predetermined substantially linear relationship existing between the reduced compression-phase measurement and the strength of the bond.

Other and further aspects of the present invention will become apparent during the course of the following description and by reference to the accompanying drawings.

BRIEF DESCRIPTION OF THE DRAWINGS

Referring now to the drawings, in which like numerals represent like parts in the several views.

DETAILED DESCRIPTION

The present invention is described primarily for use with a thermocompression bonder. However, it will be understood that such description is exemplary only, and is for the purposes of exposition and not for purposes of limitation. It will be readily appreciated that the inventive concept described is equally operative with any adhesion bonding apparatus where stress waves are emitted during the bonding cycle from two materials being bonded together.

Figure 1:
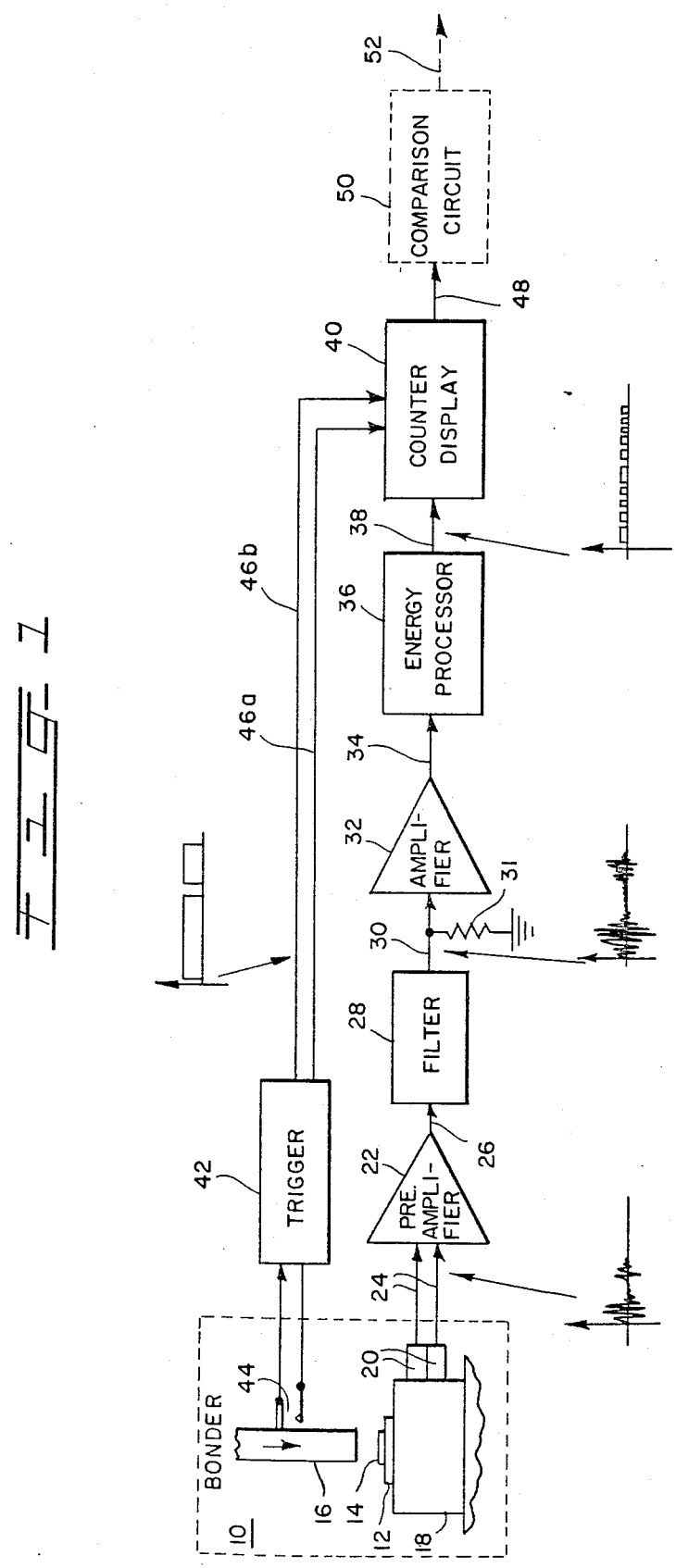
FIG. 1 is a simplified block diagram of a system for determining the strength of an adhesion bond according to the present invention.

Referring now to FIG. 1, a first article 12, as for example, a metallized substrate, and a second article 14, as for example, a lead frame, are positioned to be bonded together both below a thermode 16 and on the base 18 of a thermocompression bonder 10. When thermocompression bonder 10 is activated, thermode 16 moves longitudinally in the direction indicated in FIG. 1 to engage the surface of second article 14 and concurrently apply sufficient bonding temperature and pressure to the interface between articles 12 and 14 to bond the articles together.

Stress waves emitted from the bonding area during the bonding cycle are detected by a piezoelectric differential transducer 20 (hereinafter referred to as sensor 20) of the present bond evaluation apparatus. Sensor 20 is shown as mechanically coupled to base 18 for non-contact detection purposes, but could also, for instance, be mechanically coupled to article 12 or 14, or to thermode 16. Sensor 20, however, should only be coupled to base 18 or to thermode 16 when base 18 or thermode 16 comprises a material having a bulk sonic velocity which closely corresponds to the velocity of sound in the material of articles 12 and 14.

The signals which are detected by sensor 20 comprise mechanical waves which are: (a) generated by other electrical and mechanical components in proximity to the system of FIG. 1, but not shown; (b) generated in articles 12 and 14, or sensor 20 due to nontransient factors such as temperature and strain variations; and (c) stress waves, comprising bulk and surface waves, propagating from the bonding area in articles 12 and 14, while the articles are being bonded.

During the bonding cycle, energy is released from the bonding area in the form of stress waves, which waves, in turn, along with the possible unwanted mechanical waves generated by other electrical and mechanical components and in articles 12 and 14, as indicated above, excite sensor 20. Depending on wave damping at the interfaces, the traveling mechanical stress impulses will cause sensor 20 to provide output voltage changes which are almost proportional to the amplitude of the impulses. Sensor 20, however, should preferably be chosen to have a natural frequency, which can be any frequency as, for example, 1 megahertz, which falls both within the frequency range of the emitted stress waves from the bonding area but preferably outside the frequency range of the unwanted mechanical waves generated by other sources. In this manner sensor 20 acts as a filter to generate an electrical output signal primarily representative of the stress waves emitted from the bonding area and possibly including a very small component of the substantially attenuated unwanted mechanical waves from other sources. Because of the low amplitude of the stress-wave pulses, being found to be smaller approximately by one order of magnitude from that emitted from a substrate crack, good transmission of the mechanical wave or amplification of the sensor's output voltage is necessary.

As shown in FIG. 1, sensor 20 is connected to a low-noise preamplifier 22 by leads 24. Preamplifier 22 should be of a design having a sensitivity which is preferably in the range of 1–4 $\mu$V, but can include a sensitivity beyond this range. In any case, preamplifier 22 should be sufficiently sensitive for the particular application.

The output from preamplifier 22 is transmitted over lead 26 to a band-pass filter 28 which has a pass band that falls at least partially within the natural frequency of sensor 20, but which falls outside the range of noise frequencies generated by other components in proximity to the system. Filter 28, therefore, functions to only pass the amplified electrical signals from sensor 20 representative of the stress waves from the bonding area while simultaneously eliminating any amplified electrical signal from sensor 20 representative of the unwanted mechanical waves from other sources. Filter 28 is preferably a fifth order, or higher, high-pass filter which is commercially available. The output of filter 28 on lead 30 is further amplified by an amplifier 32. A resistor 31 is preferably added to line 30, as shown, to match the input impedance of amplifier 32. Amplifier 32 is of a design which advantageously has a fast slewing rate, such as, for example, a commercially available model 715 operational amplifier. The output of amplifier 32 is transmitted over lead 34 to an energy processor 36.

Energy processor 36 receives the amplifier and filtered signal on lead 34 and encodes the stress-wave signal released from the bonding area during both the bonding interval (compression phase) and the post-bond interval (pressure-relief interval) into a digital signal.

Energy processor 36 can comprise circuitry which operates in accordance with a very fast analog-to-digital conversion scheme. Such circuitry, however, is generally very expensive.

Figure 2:
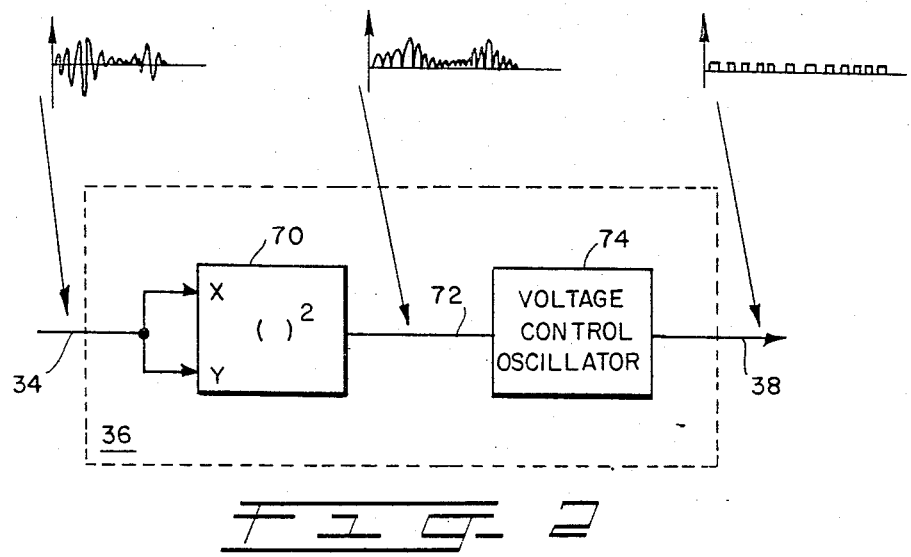
FIG. 2 is a simplified block diagram of an arrangement for the energy processor of FIG. 1.
Figure 3:
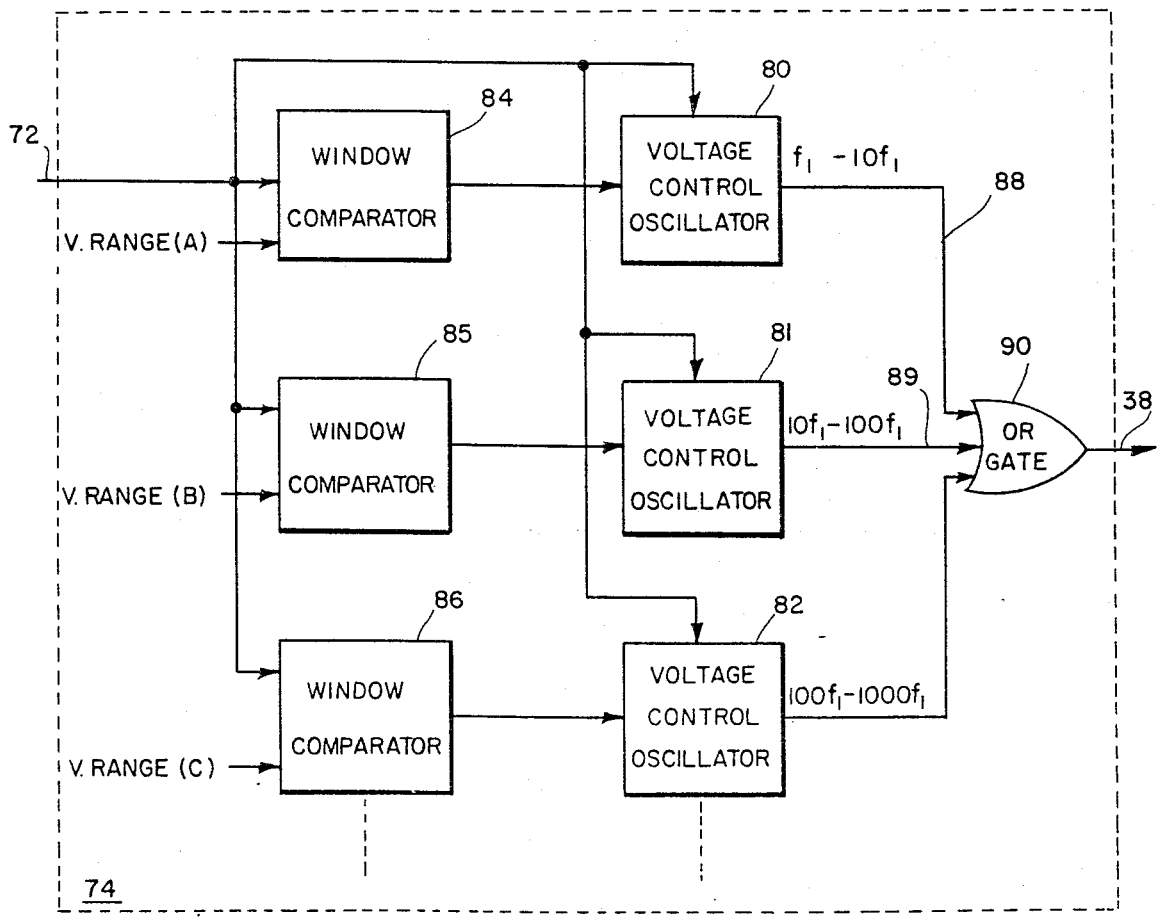
FIG. 3 is a simplified block diagram of a voltage control oscillator circuit for use in the energy processor of FIG. 2.

FIGS. 2 and 3 illustrate an energy processor 36 which comprises very fast yet relatively inexpensive circuitry capable of use in the present adhesion bond evaluation system. Energy processor 36 is shown as including a multiplier circuit 70 which provides an output signal on lead 72 that is the square of the input signal on lead 34, and a voltage-control oscillator 74. Multiplier 70 can comprise any number of circuits such as, for example, a model 4456 multiplier from Teledyne-Philbric of Dedham, Mass. voltage-control oscillator 74 functions to convert the squared amplitude-modulated input signal on lead 72 into a digital frequency-modulated (FM) output signal, a change in the amplitude of the input signal causing a corresponding change in the rate, or frequency, of the digital pulses in the output signal.

Voltage-control oscillator 74 should preferably comprise circuitry which provides a frequency range of approximately 1000:1. Since conventional voltage-control oscillators generally provide a frequency range of up to 10:1, the novel voltage-control oscillator circuitry 74 of FIG. 3 is preferably used in the present system. There, separate, commercially available voltage-control oscillators (VCO) 80, 81, and 82 provide a digital FM output signal within the range of $f_1$ to $10f_1$, $10f_1$ to $100f_1$, and $100f_1$ to $1000f_1$, respectively. Frequency $f_1$ can comprise any frequency as, for example, 1 kilohertz. Each VCO 80, 81, and 82 has a separate respective window comparator 84, 85, and 86 associated therewith. Each window comparator 84, 85, and 86 compares the instantaneous voltage level of the input signal on lead 72 with a different portion of the overall input signal voltage amplitude range and provides an enable signal to the associated VCO 80–82 when the input voltage level falls within the associated amplitude voltage range A, B, or C under comparison. For example, if the maximum input signal voltage amplitude range is found to be 1.5v, then window comparators 84, 85 and 86 might compare the input voltage level with a voltage amplitude range of 0–0.5v (Range A), 0.5–1.0v (Range B), and 1.0–1.5v (Range C), respectively. The input signal on lead 72 is also supplied to each of the VCOs 80–82.

In operation, if the input signal on lead 72 is assumed to include a voltage level which is rising through the entire ranges A and B, then window comparator 84 supplies an enable signal to VCO 80 for as long as the input voltage level is rising within range A. The enable signal from window comparator 84 causes VCO 80 to generate a digital FM output signal on lead 88 which increases in frequency from $f_1$ to $10f_1$ as the input voltage level correspondingly increases through range A. When the input voltage level reaches the lower edge of range B, window comparator 84 ceases to generate an enable signal to VCO 80 and window comparator 85 now supplies an enable signal to VCO 81. The enable signal from window comparator 85 causes VCO 81 to generate a digital FM output signal on lead 89 which increases in frequency from $10f_1$ to $100f_1$ as the input voltage level correspondingly increases through range B.

The output from each of VCOs 80–82 is coupled to a common OR-gate 90 and onto lead 38 for transmission to counter-display circuit 40. Thus, the output signal from VCO circuitry 74 can comprise serial pulses ranging in frequency between the frequency $f_1$ and the frequency $1000f_1$ in direct correspondence with voltage amplitude variations in the input signal to VCO circuitry 74 over the maximum input signal amplitude range including ranges A–C. It is, of course, possible to add further window comparators and VCOs in a manner shown in FIG. 3 to extend the range of operation. The voltage-control oscillator circuitry 74 advantageously avoids the use of integrators which are generally limited in bandwidth and accuracy.

The digital FM output signal from energy processor 36 is transmitted over lead 38 to a counter display circuit 40. Counter display circuit 40 functions to separately count the input digital pulses relating to, (a) stress waves emitted from the bonding area during the compression phase of the formation of the bond (when thermode 16 is applying heat and pressure), and (b) stress waves emitted during the pressure-relief interval occurring as thermode 16 begins to move in a direction opposite that shown in FIG. 1 at the end of the bonding cycle.

Figure 4:
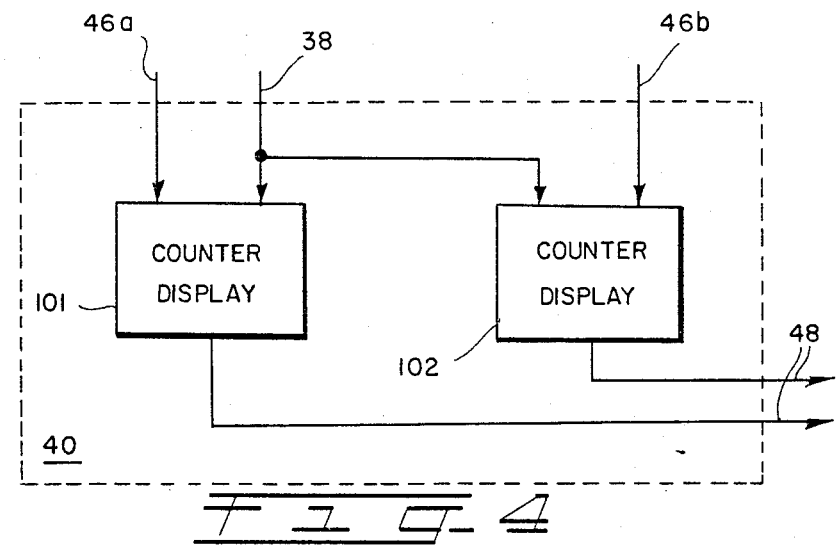
FIG. 4 is a simplified block diagram of an arrangement for the counter-display circuit of FIG. 1.

A typical arrangement for counter-display circuit 40 is shown in FIG. 4 as comprising two counters 101 and 102. The digital signal on lead 38 from energy processor 36 is applied to one input of each of counters 101 and 102. Counters 101 and 102, once enabled, count the digital pulses received on lead 38 relating to stress-wave energy emitted during the compression phase and the stress-wave energy emitted during the pressure-relief interval at the end of the bonding cycle, respectively. A trigger circuit 42, of any well-known design, functions to provide properly timed enable pulses to each of counters 101 and 102 for measuring the stress-wave energy during each of the two intervals of interest.

In operation, as thermode 16 engages the surface of article 14 to apply as sufficient bonding temperature and pressure at the interface between articles 12 and 14, a signaling means 44, which can comprise any well-known means, such as, for example, a switch activated by thermode 16, signals trigger circuit 42 that the bonding cycle is commencing. In response to the signal from signaling means 44, trigger circuit 42 is energized and transmits an enable signal, which is continuous over at least the part of the bonding cycle which includes the compression phase during the formation of the bond, to counter 101 over lead 46a. In this manner, the stress-wave energy emitted from the bonding area during the compression phase is measured in counter 101. At the end of the bonding cycle, signaling means 44 generates a second signal to trigger circuit 42 indicating that thermode 16 is beginning, or is about to begin, movement in a direction opposite that shown in FIG. 1. Such upward movement of thermode 16 relieves the pressure in the bonding area thereby causing a certain amount of stress waves to be emitted. In response to the second signal from signaling means 44, trigger circuit 42 disables counter 101 and transmits an enable signal to counter 102 over lead 46b. In this manner, the stress-wave energy emitted during the pressure-relief interval is measured in counter 102.

Figure 5:
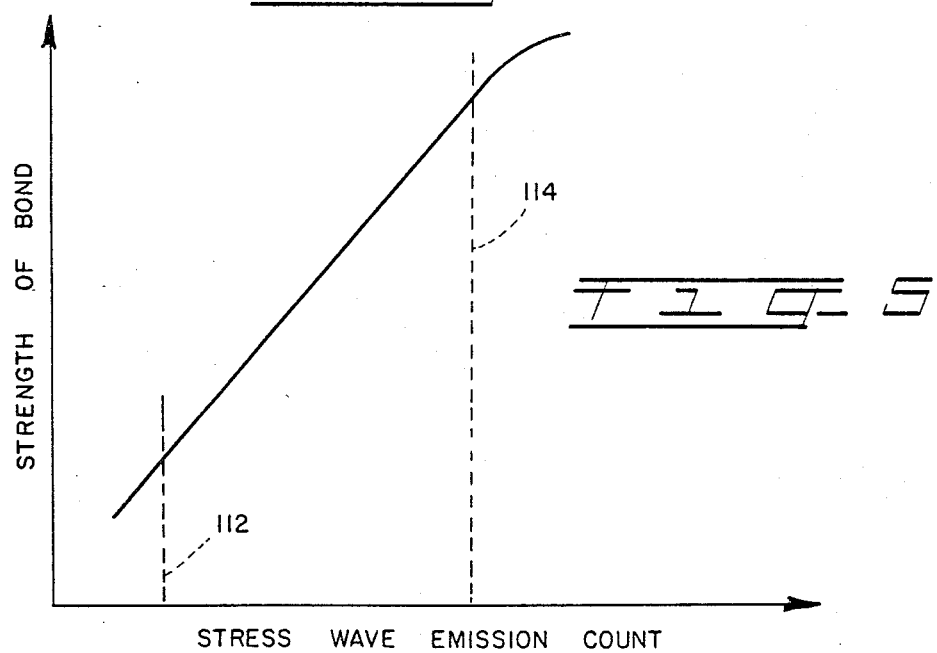
FIG. 5 is a graph illustrating the relationship between the measured stress-wave energy emitted during the bonding cycle and the strength of the adhesion bond.

As shown in FIG. 5, it was found that a substantially linear relationship exists between the strength of an adhesion bond and the stress-wave energy emitted during the formation of the bond, especially in the area of interest between lines 112 and 114 where the stress-wave measurement for most adhesion bonds are found. The relationship beyond line 114 was found to deviate somewhat from linearity in the area where the strength of the bond approaches the strength of the weakest material being bonded.

To initially obtain the curve of FIG. 5 for a particular adhesion bond, a number of sample bonds should be formed preferably under ideal conditions and the stress-wave energy for each of the sample bonds measured for the compression phase and pressure-relief intervals as described hereinbefore. The strength of each sample bond is next determined using a standard peel test. Under ideal bonding conditions, the pressure-relief measurements obtained in counter 102 should be approximately the same for each sample bond, therreby providing a predetermined pressure-relief threshold value for furture use, as will be explained hereinafter. Having measured the strength of each sample bond and the stress-wave energy emitted during the compression phase in counter 101, the curve as shown in FIG. 5 can be plotted for the determined pressure-relief threshold value.

Figure 6:
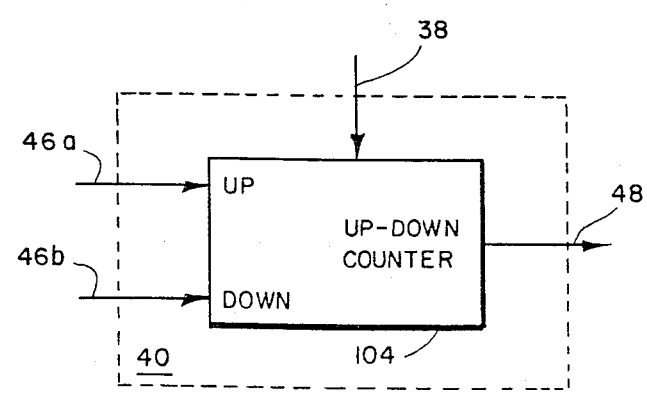
FIG. 6 is a simplified block diagram of another arrangement for the counter display circuit of FIG. 1.

For subsequently determining the strength of an adhesion bond, if the stress-wave energy measurement in counter 102, for the pressure-relief interval, exceeds the predetermined pressure-relief threshold value, as might occur when one or both of the materials at the bond interface are contaminated, then the magnitude of the difference between the measurement in counter 102 and the pressure-relief threshold value should be subtracted from the measurement obtained in counter 101. The resultant net value can then be used with the curve of FIG. 5 to determine the strength of the bond and whether such bond is acceptable or not. From the above explanation, it can be seen that the measurements in counters 101 and 102 can be used to determine the cause of an unacceptable bond. For instance, a lower than normal count in counter 101 could indicate that bonder 10 had provided an insufficient amount of temperature or pressure, whereas a higher than normal measurement in counter 102 could indicate possible material contamination in the bonding area. For automatic operation, an electrical signal indicating the measurements in counters 101 and 102 can be transmitted on leads 48 to any well-known comparison circuit 50 which functions to compare the signal from counter 102 with the predetermined pressure-relief threshold value and subtract any difference therebetween from the measurement in counter 101. Comparision circuit 50 can also comprise circuitry which indicates, (a) the net resultant value, (b) the strength of the bond, and (c) audibly or visually whether the bond is acceptable or not or generates a signal on lead 52 to an audible or visual indication means (not shown).

Where it may not be necessary or desirable to record or display the individual stress-wave energy measurements for the compression phase and pressure-relief intervals of a bond, the counter-display circuit 40 of FIG. 6 may be substituted for the counter-display circuit of FIG. 4. There, an up-down counter 104 replaces both of the counters 101 and 102 of FIG. 4. In operation, during the compression phase, when trigger circuit 42 is transmitting an enable signal on lead 46a, counter 104 counts the number or pulses received on lead 38 from energy processor 36 in an increasing fashion. When trigger circuit next transmits an enable signal on lead 46b, during the pressure-relief interval, counter 104 then subtracts each pulse received on lead 38 from the total count obtained during the compression-phase interval. The ultimate count obtained, therefore, provides a measurement of the difference in the stress-wave energy emitted during the compression phase and the pressure-relief intervals of an adhesion bond. This difference can then be used to determine the strength of the bond. It must be cautioned, however, that the difference value measured with the circuit of FIG. 6 should not be correlated with the curve of FIG. 5 obtained with the circuit of FIG. 4. Instead, a new curve should be prepared using both the present system of FIG. 1 with the counter display 40 of FIG. 6 and the procedure outlined hereinbefore for obtaining the necessary data to plot the curve of FIG. 5. The underlying reason for not using the curve obtained with the counter-display circuit of FIG. 4 with the circuit of FIG. 6 is that the curve of FIG. 5, as obtained with the counter-display circuit of FIG. 4, is displaced from the curve of FIG. 5 obtained using the counter-display circuit of FIG. 6 by an amount generally equal to the predetermined pressure-relief threshold value.

For automatic operation, the difference value obtained in counter 104 of FIG. 6 can be transmitted on lead 48 to any one of a number of suitable comparison means 50 for comparing the difference value with a predetermined stress-wave emission count threshold value indicating a minimal acceptable bond strength, thereby to indicate the acceptability of each bond. Comparison means 50 can, of course, advantageously include circuitry for generating a go-no-go signal on lead 52 to an audible or visual means (not shown) for indicating an acceptable or unacceptable adhesion bond, and for providing a visual indication of the strength of a bond.

It is, of course, to be understood that where accurate adhesion bond strength measurements are not required it is possible to only measure the stress-wave energy emitted during the formation of the bond and compare this measurement with a substantially linear relationship, as shown in FIG. 5, obtained in a manner similar to that described hereinabove. For such arrangement, counter-display circuit 40 need only comprise counter 101 of FIG. 4, and trigger circuit 42 need only supply an enable signal on lead 46a.

It is to be understood that the above-described embodiments are simply illustrative of the principles of the invention. Various other modifications and changes may be made by those skilled in the art which will embody the principles of the invention and fall within the spirit and scope thereof.

What is claimed is:

1. A method for the real-time, non-destructive evaluation of the strength of an adhesion bond the formation of which includes a compression phase using stress-wave emission techniques, comprising the steps of:
   a. measuring the stress-wave energy emitted from the bonding area during the compression phase; and
   b. determining the strength of the adhesion bond by comparing the measured stress-wave energy with a predetermined substantially linear relationship between the emitted stress-wave energy and the strength of the particular type of adhesion bond being formed.

2. A method for the real-time, non-destructive evaluation of the strength of an adhesion bond the formation of which includes a compression phase and a pressure-relief interval using stress-wave emission techniques, comprising the steps of:
   a. measuring the stress-wave energy emitted from a bonding area during the compression phase;
   b. measuring the stress-wave energy emitted from the bonding area during the pressure-relief interval at the end of the bonding cycle;
   c. determining the magnitude of the difference between the stress-wave energy measurements obtained during said compression phase and said pressure-relief interval; and
   d. determining the strength of said bond by comparing said difference magnitude obtained in step (c) with a predetermined substantially linear relationship between the determined difference magnitude and the strength of the particular type of adhesion bond being formed.

3. A method according to claim 2 comprising the additional step of:
   e. generating a signal indicative of an acceptable bond when said difference magnitude exceeds a predetermined threshold value.

4. A method for the real-time, non-destructive evaluation of the strength of an adhesion bond the formation of which includes a compression phase and a pressure-relief interval using stress-wave emission techniques, comprising the steps of:
   a. measuring the stress-wave energy emitted from a bonding area during the compression phase interval;
   b. measuring the stress-wave energy emitted from the bonding area during a pressure-relief interval at the end of a bonding cycle;
   c. subtracting a predetermined pressure-relief threshold value from said pressure-relief interval measurement obtained in step (b) to obtain an excess value;
   d. decreasing the stress-wave measurement obtained for said compression phase interval by the amount of said excess value determined in step (c); and
   e. determining the strength of said adhesion bond by comparing said decreased stress-wave measurement obtained in step (d) with a predetermined substantially linear relationship between the decreased compression-phase interval stress-wave energy measurement and the strength of the particular type of adhesion bond being formed.

5. A method according to claim 4 comprising the additional step of:

f. providing either one of a visual and audible indication of an acceptable bond when said decreased stress-wave measurement obtained in step (d) exceeds a predetermined second threshold level.

6. Apparatus for detecting and measuring stress waves emitted during the adhesion bonding of a first article to a second article the formation of which includes a compression phase and a pressure-relief interval for the real-time non-destructive evaluation of the adhesion bond, the apparatus comprising:
   a. a sensor for detecting stress waves propagating in the material of the articles and for generating an electrical output representative of the detected waves;
   b. a first signal-processing means comprising:
      i. an amplifier for amplifying the electrical output from said sensor; and
      ii. a band-pass filter connected to the output of said amplifier for generating an output signal within a pass-band falling outside the range of frequencies normally generated by components in proximity to the apparatus; and
   c. second signal-processing means connected to the output of said first signal-processing means, comprising:
      i. means for measuring the magnitude of the stress-wave energy emitted from the bonding area during at least the compression phase interval; and
      ii. comparing means connected to the output of said measuring means for comparing a resultant stress-wave energy value output signal from said measuring means with a predetermined substantially linear relationship between said resultant stress-wave energy value and the strength of said adhesion bond.

7. Apparatus according to claim 6 wherein said measuring means comprises circuitry for generating an output signal indicative of said resultant stress-wave energy value, said resultant energy value being equal to the stress-wave energy value measured during the compression phase interval.

8. Apparatus according to claim 7 wherein said second signal-processing comparing means further comprises means for generating an output signal indicative of an acceptable bond when said resultant stress-wave energy value exceeds a predetermined threshold value.

9. Apparatus according to claim 6 wherein said second signal-processing measuring means comprises circuitry for measuring the stress-wave energy emitted from the bonding area during both the compression phase and the pressure-relief interval of the adhesion bond, determining the amount that the stress-wave energy measured for said pressure-relief interval exceeds a predetermined pressure-relief threshold value, and reducing the stress-wave energy measurement for said compression-phase interval by an amount equal to said excess amount to arrive at a resultant stress-wave energy value.

10. Apparatus according to claim 9 wherein said second signal-processing comparing means further comprises circuitry for generating an outout signal indicative of an acceptable bond when said resultant stress-wave energy value exceeds a second predetermined threshold value.

11. Apparatus according to claim 6 wherein:
   said second signal-processing measuring means comprises circuitry for measuring the stress-wave energy emitted from the bonding area during both the compression phase and the pressure-relief interval of the adhesion bond and reducing said measured stress-wave energy for said compression phase interval by an amount equal to said measured stress-wave energy for said pressure-relief interval to obtain a resultant stress-wave energy value.

12. Apparatus according to claim 11 wherein:
   said second signal-processing comparing means further comprises circuitry for generating an electrical output signal indicative of an acceptable bond when said resultant stress-wave energy value exceeds a predetermined threshold value.

* * * * *